(12) United States Patent
Sharpe et al.

(10) Patent No.: US 6,681,998 B2
(45) Date of Patent: Jan. 27, 2004

(54) AEROSOL GENERATOR HAVING INDUCTIVE HEATER AND METHOD OF USE THEREOF

(75) Inventors: David E. Sharpe, Chesterfield, VA (US); John L. Felter, Chester, VA (US)

(73) Assignee: Chrysalis Technologies Incorporated, Richmond, VA (US)

( * ) Notice: Subject to any disclaimer, the term of this patent is extended or adjusted under 35 U.S.C. 154(b) by 0 days.

(21) Appl. No.: 09/742,323

(22) Filed: Dec. 22, 2000

(65) Prior Publication Data

US 2002/0078956 A1 Jun. 27, 2002

(51) Int. Cl.$^7$ ................................. B05B 1/24
(52) U.S. Cl. ................ 239/13; 239/135; 239/136; 128/203.26; 128/203.27; 392/314; 392/324; 219/628; 219/629; 219/630; 219/674
(58) Field of Search ................ 239/13, 86, 128, 239/133, 135, 136, 600; 128/203.25, 203.26, 203.17, 203.27; 392/314, 318, 324, 338; 219/600, 601, 618, 628, 629, 630, 672, 674

(56) References Cited

U.S. PATENT DOCUMENTS

| | | |
|---|---|---|
| 2,896,856 A | 7/1959 | Kravits |
| 3,084,698 A | 4/1963 | Smith |
| 3,157,179 A | 11/1964 | Paullus et al. |
| 3,162,324 A | 12/1964 | Houser |
| 3,431,393 A | 3/1969 | Katsuda |
| 3,486,663 A | 12/1969 | Humphrey |
| 3,658,059 A | 4/1972 | Steil |
| 3,716,416 A | 2/1973 | Adlhart et al. |
| 3,750,961 A | 8/1973 | Franz |
| 3,847,304 A | 11/1974 | Cohen |
| 3,859,398 A | 1/1975 | Havstad |
| 3,902,635 A | 9/1975 | Jinotti |
| 3,903,883 A | 9/1975 | Pecina et al. |
| 3,904,083 A | 9/1975 | Little |
| 3,967,001 A | 6/1976 | Almaula et al. |

(List continued on next page.)

FOREIGN PATENT DOCUMENTS

| | | |
|---|---|---|
| BE | 354004 A | 9/1928 |
| BE | 354094 A | 9/1928 |
| DE | 1036470 B1 | 8/1958 |
| EP | 0358114 A | 3/1990 |
| EP | 0642802 A2 | 5/1996 |
| FR | 667979 A | 10/1929 |
| HU | 168128 B | 11/1977 |
| HU | 216121 B | 3/1991 |
| HU | 207457 A | 4/1993 |
| HU | P953409 | 6/1994 |
| WO | 94/09842 A | 5/1994 |
| WO | 98/17131 | 4/1998 |

OTHER PUBLICATIONS

Notification of Transmittal of International Preliminary Examination Report for PCT/US01/44812 dated Mar. 4, 2003.
Written Opinion for PCT/US01/44812 dated Sep. 26, 2002.
Notification of Transmittal of the International Search Report or the Declaration Dated May 10, 2002 for PCT/US01/44812.

(List continued on next page.)

*Primary Examiner*—Steven J. Ganey
(74) *Attorney, Agent, or Firm*—Burns, Doane, Swecker & Mathis, LLP (57) ABSTRACT

An aerosol generator includes an induction heating arrangement to vaporize fluid contained in a fluid passage. The vapor is then expelled from the fluid passage into the air creating a mist that forms the aerosol. The aerosol generator includes an excitation coil that inductively heats a heating element which transfers heat to the fluid in the fluid passage. The fluid passage can be located in a metal tube which can be removably mounted in the aerosol generator.

29 Claims, 4 Drawing Sheets

U.S. PATENT DOCUMENTS

| | | |
|---|---|---|
| 3,987,941 A | 10/1976 | Blessing |
| 3,993,246 A | 11/1976 | Erb et al. |
| 4,042,153 A | 8/1977 | Callahan et al. |
| 4,060,082 A | 11/1977 | Lindberg et al. |
| 4,077,542 A | 3/1978 | Petterson |
| 4,161,282 A | 7/1979 | Erb et al. |
| 4,162,501 A | 7/1979 | Mitchell et al. |
| 4,215,708 A | 8/1980 | Bron |
| 4,231,492 A | 11/1980 | Rios |
| 4,258,073 A | 3/1981 | Payne |
| 4,261,356 A | 4/1981 | Turner et al. |
| 4,289,003 A | 9/1981 | Yang |
| 4,291,838 A | 9/1981 | Williams |
| 4,303,083 A | 12/1981 | Burruss, Jr. |
| 4,383,171 A | 5/1983 | Sinha et al. |
| 4,391,308 A | 7/1983 | Steiner |
| 4,395,303 A | 7/1983 | Weir |
| 4,433,797 A | 2/1984 | Galia |
| 4,471,892 A | 9/1984 | Coleman |
| 4,512,341 A | 4/1985 | Lester |
| 4,558,196 A * | 12/1985 | Babasade ............ 219/629 |
| 4,575,609 A | 3/1986 | Fassel et al. |
| 4,627,432 A | 12/1986 | Newell et al. |
| 4,649,911 A | 3/1987 | Knight et al. |
| 4,682,010 A | 7/1987 | Drapeau et al. |
| 4,695,625 A | 9/1987 | Macdonald |
| 4,700,657 A | 10/1987 | Butland |
| 4,730,111 A | 3/1988 | Vestal et al. |
| 4,735,217 A | 4/1988 | Gerth et al. |
| 4,744,932 A | 5/1988 | Browne |
| 4,749,778 A | 6/1988 | Fukuzawa et al. |
| 4,762,995 A | 8/1988 | Browner et al. |
| 4,764,660 A * | 8/1988 | Swiatosz ............ 239/136 |
| 4,771,563 A * | 9/1988 | Easley ............ 239/136 |
| 4,776,515 A | 10/1988 | Michalchik |
| 4,790,305 A | 12/1988 | Zoltan et al. |
| 4,811,731 A | 3/1989 | Newell et al. |
| 4,819,625 A | 4/1989 | Howe |
| 4,819,834 A | 4/1989 | Thiel |
| 4,829,996 A | 5/1989 | Noakes et al. |
| 4,837,260 A | 6/1989 | Sato et al. |
| 4,848,374 A | 7/1989 | Chard et al. |
| 4,871,115 A | 10/1989 | Hessey |
| 4,871,623 A | 10/1989 | Hoopman et al. |
| 4,877,989 A | 10/1989 | Drews et al. |
| 4,911,157 A | 3/1990 | Miller |
| 4,922,901 A | 5/1990 | Brooks et al. |
| 4,926,852 A | 5/1990 | Zoltan et al. |
| 4,935,624 A | 6/1990 | Henion et al. |
| 4,941,483 A | 7/1990 | Ridings et al. |
| 4,947,875 A | 8/1990 | Brooks et al. |
| 4,974,754 A | 12/1990 | Wirz |
| 4,982,097 A | 1/1991 | Slivon et al. |
| 4,992,206 A | 2/1991 | Waldron |
| 5,021,802 A | 6/1991 | Allred |
| 5,044,565 A | 9/1991 | Alexander |
| 5,056,511 A | 10/1991 | Ronge |
| 5,060,671 A | 10/1991 | Counts et al. |
| 5,063,921 A | 11/1991 | Howe |
| 5,096,092 A | 3/1992 | Devine |
| 5,117,482 A * | 5/1992 | Hauber ............ 239/135 |
| 5,125,441 A | 6/1992 | Mette |
| 5,133,343 A | 7/1992 | Johnson, IV et al. |
| 5,134,993 A | 8/1992 | van der Linden et al. |
| 5,135,009 A | 8/1992 | Müller et al. |
| 5,144,962 A | 9/1992 | Counts et al. |
| 5,151,827 A | 9/1992 | Ven et al. |
| 5,178,305 A | 1/1993 | Keller |
| 5,184,776 A | 2/1993 | Minier |
| 5,211,845 A * | 5/1993 | Kaneshige ............ 219/628 |
| 5,217,004 A | 6/1993 | Blasnik et al. |
| 5,222,185 A * | 6/1993 | McCord, Jr. ............ 219/630 |
| 5,226,441 A | 7/1993 | Dunmire et al. |
| 5,228,444 A | 7/1993 | Burch |
| 5,230,445 A | 7/1993 | Rusnak |
| 5,231,983 A | 8/1993 | Matson et al. |
| 5,259,370 A | 11/1993 | Howe |
| 5,290,540 A | 3/1994 | Prince et al. |
| 5,298,744 A | 3/1994 | Mimura et al. |
| 5,299,565 A | 4/1994 | Brown |
| 5,322,057 A | 6/1994 | Raabe et al. |
| 5,327,915 A | 7/1994 | Porenski et al. |
| 5,342,180 A | 8/1994 | Daoud |
| 5,342,645 A | 8/1994 | Eisele et al. |
| 5,349,946 A | 9/1994 | McComb |
| 5,395,445 A | 3/1995 | Bohanan |
| 5,421,489 A | 6/1995 | Holzner, Sr. et al. |
| 5,462,597 A | 10/1995 | Jubran |
| 5,474,059 A | 12/1995 | Cooper |
| 5,515,842 A | 5/1996 | Ramseyer et al. |
| 5,522,385 A | 6/1996 | Lloyd et al. |
| 5,556,964 A | 9/1996 | Hofstraat et al. |
| 5,564,442 A | 10/1996 | MacDonald et al. |
| 5,565,677 A | 10/1996 | Wexler |
| 5,575,929 A | 11/1996 | Yu et al. |
| 5,585,045 A | 12/1996 | Heinonen et al. |
| 5,617,844 A | 4/1997 | King |
| 5,642,728 A | 7/1997 | Andersson et al. |
| 5,674,860 A | 10/1997 | Carling et al. |
| 5,682,874 A | 11/1997 | Grabenkort et al. |
| 5,730,158 A | 3/1998 | Collins et al. |
| 5,743,251 A | 4/1998 | Howell et al. |
| 5,756,995 A | 5/1998 | Maswadeh et al. |
| 5,765,724 A | 6/1998 | Amberg et al. |
| 5,810,988 A * | 9/1998 | Smith et al. ............ 239/135 |
| 5,823,178 A | 10/1998 | Lloyd et al. |
| 5,839,430 A | 11/1998 | Cama |
| 5,855,202 A | 1/1999 | Andrade |
| 5,856,671 A | 1/1999 | Henion et al. |
| 5,863,652 A | 1/1999 | Matsumura et al. |
| 5,869,133 A | 2/1999 | Anthony et al. |
| 5,872,010 A | 2/1999 | Karger et al. |
| 5,878,752 A | 3/1999 | Adams et al. |
| 5,881,714 A | 3/1999 | Yokoi et al. |
| 5,906,202 A | 5/1999 | Schuster et al. |
| 5,914,122 A | 6/1999 | Otterbeck et al. |
| 5,932,249 A | 8/1999 | Gruber et al. |
| 5,932,315 A | 8/1999 | Lum et al. |
| 5,934,272 A | 8/1999 | Lloyd et al. |
| 5,934,273 A | 8/1999 | Andersson et al. |
| 5,944,025 A | 8/1999 | Cook et al. |
| 5,954,979 A | 9/1999 | Counts et al. |
| 5,957,124 A | 9/1999 | Lloyd et al. |
| 5,970,973 A | 10/1999 | Gonda et al. |
| 5,970,974 A | 10/1999 | Van Der Linden et al. |
| 5,978,548 A | 11/1999 | Holmstrand et al. |
| 5,990,465 A * | 11/1999 | Nakaoka et al. ............ 219/630 |
| 5,993,633 A | 11/1999 | Smith et al. |
| 6,014,970 A | 1/2000 | Ivri et al. |
| 6,053,176 A | 4/2000 | Adams et al. |
| 6,054,032 A | 4/2000 | Haddad et al. |
| 6,069,214 A | 5/2000 | McCormick et al. |
| 6,069,219 A | 5/2000 | McCormick et al. |
| 6,070,575 A | 6/2000 | Gonda et al. |
| 6,071,428 A | 6/2000 | Franks et al. |
| 6,076,522 A | 6/2000 | Dwivedi et al. |
| 6,077,543 A | 6/2000 | Gordon et al. |
| 6,080,721 A | 6/2000 | Patton |
| 6,085,740 A | 7/2000 | Ivri et al. |
| 6,085,753 A | 7/2000 | Gonda et al. |
| 6,089,228 A | 7/2000 | Smith et al. |

| | | |
|---|---|---|
| 6,095,153 A | 8/2000 | Kessler et al. |
| 6,098,615 A | 8/2000 | Lloyd et al. |
| 6,098,620 A | 8/2000 | Lloyd et al. |
| 6,103,270 A | 8/2000 | Johnson et al. |
| 6,116,516 A | 9/2000 | Gañán-Calvo |
| 6,116,893 A | 9/2000 | Peach |
| 6,119,953 A | 9/2000 | Gañán-Calvo et al. |
| 6,123,068 A | 9/2000 | Lloyd et al. |
| 6,123,936 A | 9/2000 | Platz et al. |
| 6,131,567 A | 10/2000 | Gonda et al. |
| 6,131,570 A | 10/2000 | Schuster et al. |
| 6,136,346 A | 10/2000 | Eljamal et al. |
| 6,138,668 A | 10/2000 | Patton et al. |
| 6,147,336 A * | 11/2000 | Ushijima et al. ........... 219/629 |
| 6,155,268 A | 12/2000 | Takeuchi |
| 6,158,431 A | 12/2000 | Poole |
| 6,158,676 A | 12/2000 | Hughes |
| 6,159,188 A | 12/2000 | Laibovitz et al. |
| 6,164,630 A | 12/2000 | Birdsell et al. |
| 6,165,463 A | 12/2000 | Platz et al. |
| 6,167,880 B1 | 1/2001 | Gonda et al. |
| 6,174,469 B1 | 1/2001 | Gañán-Calvo |
| 6,182,712 B1 | 2/2001 | Stout et al. |
| 6,187,214 B1 | 2/2001 | Gañán-Calvo |
| 6,187,344 B1 | 2/2001 | Eljamal et al. |
| 6,189,803 B1 | 2/2001 | Gañán-Calvo |
| 6,192,882 B1 | 2/2001 | Gonda |
| 6,197,835 B1 | 3/2001 | Gañán-Calvo |
| 6,205,999 B1 | 3/2001 | Ivri et al. |
| 6,206,242 B1 | 3/2001 | Amberg et al. |
| 6,207,135 B1 | 3/2001 | Rössling et al. |
| 6,223,746 B1 | 5/2001 | Jewett et al. |
| 6,230,706 B1 | 5/2001 | Gonda et al. |
| 6,231,851 B1 | 5/2001 | Platz et al. |
| 6,234,167 B1 | 5/2001 | Cox et al. |
| 6,234,402 B1 | 5/2001 | Gañán-Calvo |
| 6,235,177 B1 | 5/2001 | Borland et al. |
| 6,250,298 B1 | 6/2001 | Gonda et al. |
| 6,257,233 B1 | 7/2001 | Burr et al. |
| 6,258,341 B1 | 7/2001 | Foster et al. |
| 6,263,872 B1 | 7/2001 | Schuster et al. |
| 6,267,155 B1 | 7/2001 | Parks et al. |
| 6,275,650 B1 | 8/2001 | Lambert |
| 6,276,347 B1 | 8/2001 | Hunt |
| 6,284,525 B1 | 9/2001 | Mathies et al. |
| 6,288,360 B1 | 9/2001 | Beste |
| 6,290,685 B1 | 9/2001 | Insley et al. |
| 6,294,204 B1 | 9/2001 | Rössling et al. |
| 6,295,986 B1 | 10/2001 | Patel et al. |
| 6,318,361 B1 | 11/2001 | Sosiak |
| 2001/0032647 A1 | 10/2001 | Schuster et al. |

OTHER PUBLICATIONS

Barry P.W. et al."In Vitro Comparison of the Amount of Salbutamol Available for Inhalation From Different Formulations Used with Different Spacer Devices" Eur Respir J 1997; 10: 1345–1348.

Byron, Peter R. Ph.D., Chairman, "Recommendations of the USP Advisory Panel on Aerosols on the USP General Chapters on Aerosols (601) and Uniformity of Dosage Units (905)", Pharmacopeial Forum, vol. 20, No. 3, pp. 7477–7505, May–Jun. 1994 (023).

Hindle, Michael et al., "High Efficiency Aerosol Production Using the Capillary Aerosol Generator" PharmSci 1998; 1: (1: suppl) S211.

Hindle, Michael et al., "High Efficiency Fine Particle Generation Using Novel Condensation Technology", Respiratory Drug Delivery VI (eds Dalby, R.N., Byron, P.R. & Farr, S.J.) Interpharm Press, Buffalo Grove, IL 1998 pp. 97–102.

Hou, Shuguang et al. *Solution Stability of Budensonide in Novel Aerosol Formulations* Abstract No. 2582, Solid State Physical Pharmacy, Nov. 17, 1998, p. S–307.

Kousaka, Yasuo et al., "Generation of Aerosol Particles by Boiling of Suspensions", Aerosol Science and Technology, 21:236–240 (1994) (023).

Morén, Folke "Drug Deposition of Pressurized Inhalation Aerosols I. Influence of Actuator Tube Design" AB Draco (Subsidiary of AB Astra, Sweden) Research and Development Laboratories Pack, S–221 01 Lund (Sweden), International Journal of Pharmaceutrics, 1 (1978) 205–212.

Newman, Stephen P. et al. "Deposition of Pressurized Suspension Aerosols Inhaled Through Extension Devices[1-3]" Am Rev Respir Dis 1981; 124:317–320.

Roth, G. et al. High Performance Liquid Chromatographic Determination of Epimers, Impurities, and Content of the Glucocorticoid Budesonide and Preparation of Primary Standard, Journal of Pharmaceutical Sciences, vol. 69, No. 7, pp. 766–770, Jul. 1980.

* cited by examiner

AEROSOL GENERATOR HAVING INDUCTIVE HEATER AND METHOD OF USE THEREOF

FIELD OF THE INVENTION

The present invention relates to aerosol generators and methods for generating an aerosol. In particular, the aerosol generators are vapor driven, thus are able to generate aerosols without requiring the use of compressed gas propellants. The present invention has particular applicability to the generation of aerosols containing medicated material.

DESCRIPTION OF RELATED ART

Aerosols are useful in a wide variety of applications. For example, it is often desirable to treat respiratory ailments with, or deliver drugs by means of, aerosol sprays of finely divided particles of liquid and/or solid, e.g., powder, medicaments, etc., which are inhaled into a patient's lungs. Aerosols are also used for purposes such as providing desired scents to rooms distributing insecticide and delivering paint and lubricant.

Various techniques are known for generating aerosols. For example, U.S. Pat. Nos. 4,811,731 and 4,627,432 disclose devices for administering medicaments to patients in which a capsule is pierced by a pin to release a medicament in powder form. A user then inhales the released medicament through an opening in the device. While such devices may be acceptable for use in delivering medicaments in powder form, they are not suited to delivering medicaments in liquid form. The devices are also, of course, not well-suited to delivery of medicaments to persons who might have difficulty in generating a sufficient flow of air through the device to properly inhale the medicaments, such as asthma sufferers. The devices are also not suited for delivery of materials in applications other than medicament delivery.

Another well-known technique for generating an aerosol involves the use of a manually operated pump which draws liquid from a reservoir and forces it through a small nozzle opening to form a fine spray. A disadvantage of such aerosol generators, at least in medicament delivery applications, is the difficulty of properly synchronizing inhalation with pumping. More importantly, however, because such aerosol generators tend to produce particles of large size, their use as inhalers is compromised because large particles tend to not penetrate deep into the lungs.

One of the more popular techniques for generating an aerosol including liquid or powder particles involves the use of a compressed propellant, often containing a chlorofluorocarbon (CFC) or methylchloroform, to entrain a material, usually by the Venturi principle. For example, inhalers containing compressed propellants such as compressed gas for entraining a medicament are often operated by depressing a button to release a short charge of the compressed propellant. The propellant entrains the medicament as the propellant flows over a reservoir of the medicament so that the propellant and the medicament can be inhaled by the user.

In propellant-based arrangements, a medicament may not be properly delivered to the patient's lungs when it is necessary for the user to time the depression of an actuator such as a button with inhalation. Moreover, aerosols generated by propellant-based arrangements may have particles that are too large to insure efficient and consistent deep lung penetration. Although propellant-based aerosol generators have wide application for uses such as antiperspirant and deodorant sprays and spray paint, their use is often limited because of the well-known adverse environmental effects of CFC's and methylchloroform, which are among the most popular propellants used in aerosol generators of this type.

In drug delivery applications, it is typically desirable to provide an aerosol having average mass median particle diameters of less than 2 microns to facilitate deep lung penetration. Most known aerosol generators are incapable of generating aerosols having average mass median particle diameters less than 2 microns. It is also desirable, in certain drug delivery applications, to deliver medicaments at high flow rates, e.g., above 1 milligram per second. Most known aerosol generators suited for drug delivery are incapable of delivering such high flow rates in the 0.2 to 2.0 micron size range.

U.S. Pat. No. 5,743,251, which is hereby incorporated by reference in its entirety, discloses an aerosol generator, along with certain principles of operation and materials used in an aerosol generator, as well as a method of producing an aerosol. The aerosol generator disclosed according to the '251 patent is a significant improvement over earlier aerosol generators, such as those used as inhaler devices.

SUMMARY OF THE INVENTION

The invention provides methods and apparatus for producing an aerosol by using inductive heating. The inductive heater heats fluid in a fluid passage so as to produce a vapor which forms an aerosol when it is exposed to the air outside the fluid passage.

The inductive heater can include one or more coils that produce an electromagnetic field when an electrical current is passed therethrough. The flux from this electromagnetic field produces eddy currents in a heating element to thereby heat the heating element and transfer heat to the fluid by use of the inductive heater.

The inductive heater can be fabricated using various materials. Preferably, the heating element has electrically conductive material associated with it. For example, the heating element can be made of metal or it can be made of glass and have a metal coating on it. A flux concentrator can optionally be used to increase the flux concentration in the heating element and thereby heat the fluid passage at a faster rate.

In a preferred embodiment, the fluid passage can be in a capillary tube that is replaceable. For example, the tube can be mounted in the aerosol generator such that it can be pulled out and replaced with a new one. In another embodiment, the fluid passage can be a channel in a multilayered composite.

BRIEF DESCRIPTION OF THE DRAWINGS

Various exemplary embodiments of this invention will be described in detail, with reference to the following figures, wherein.

DETAILED DESCRIPTION OF PREFERRED EMBODIMENTS

The invention provides an inductively heated arrangement for forming an aerosol. In particular, inductive heating is used to heat fluid to temperatures high enough to volatize the fluid. The volatized fluid is then released or expelled from the device such that when the vapor comes in contact with the cooler air outside the device, the vapor forms into miniature droplets that create an aerosol.

In order for the inductive heater to heat the fluid, a current is passed through one or more inductive heating coils which produces an electromagnetic flux. A heating element is located such that the flux produces eddy currents inside the heating element which in turn heats the heating element. This heat is then transferred to a fluid by way of direct or indirect thermal conduction.

Figure 1:
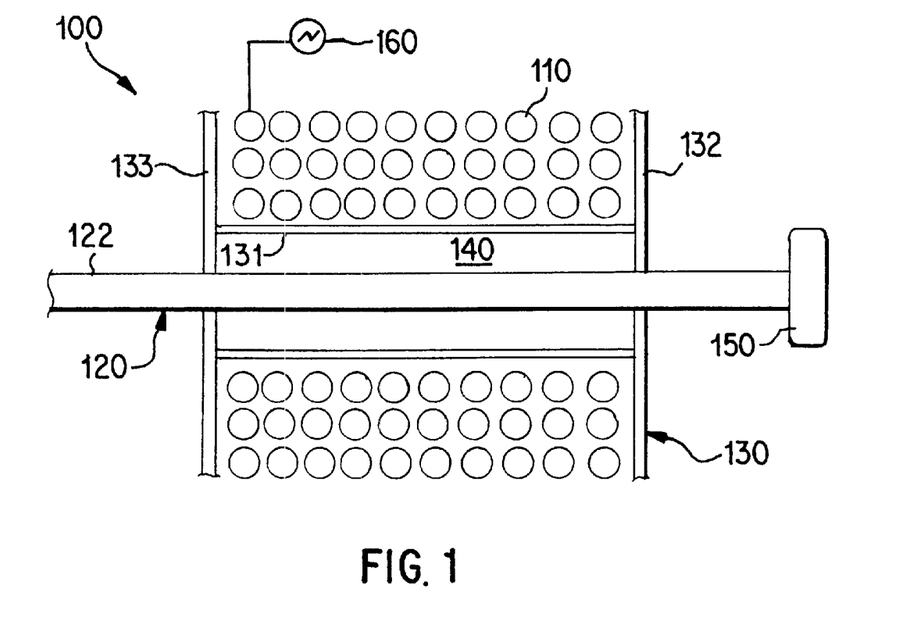
FIG. 1 is an exemplary embodiment of an inductive heater.
Figure 2:
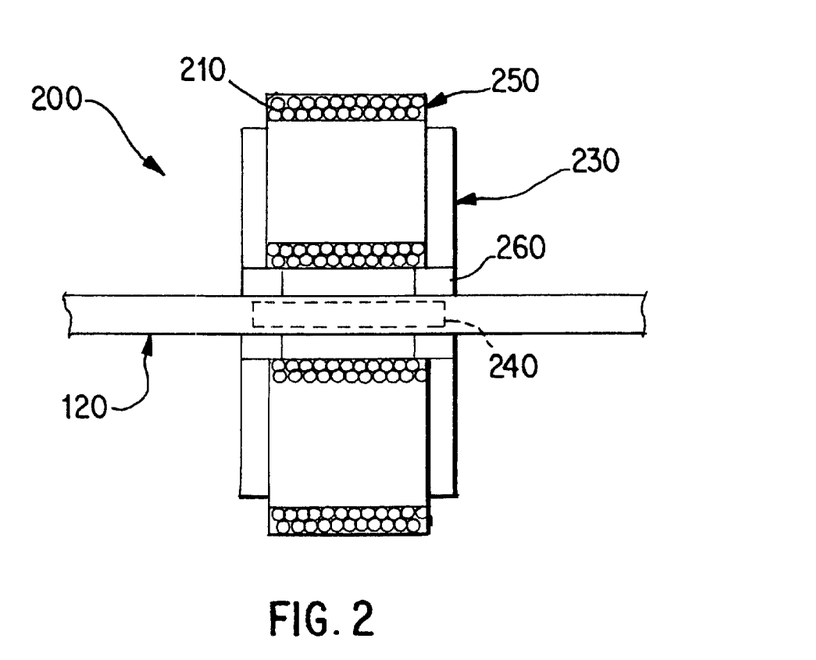
FIG. 2 is another exemplary embodiment of an inductive heater.

FIG. 1 shows details of an inductive heater 100 which can be used for heating fluid within a fluid passage 120. The fluid can be supplied to the passage 120 by a fluid source 150. The inductive heater 100 is a solenoidal inductive heater which includes excitation coils 110 wrapped around a coil bobbin 130 and a high frequency driver 160 supplies electric current to the coils 110. The coil bobbin 130 has a tubular structure 131 with two circular pieces 132 and 133 located on each end that extend from the tubular center piece 131. The coil bobbin 130 can be made of any suitable material, preferably a non-magnetic and non-electrically conductive material such as plastic or ceramic materials, e.g., a high temperature material.

Located through the middle of the center tubular piece 131 of the coil bobbin 130 is an electrically conductive heating element, which in FIG. 1 is a tube 122 (e.g., a metal tube or composite tube such as a glass tube including a metal coating or layer) which forms a fluid passage 120. The fluid passage 120 is designed so fluid can enter at one end, flow through the passageway and then exit at the other end. In operation, fluid in the fluid passage 120 is inductively heated to vaporize the fluid.

The fluid source 150 can be any fluid source capable of providing fluid to the fluid passage 120. The fluid source can be integrally formed with the inductive heater or be an external component that is removable and replaceable. The fluid source 150 can provide fluid to the fluid passage 120 by numerous means, including, but not limited to, using pressure differences to force fluid into the passage, gravity, etc.

In the operation of the inductive heater, electrical current is sent through the excitation coils 110 at a predetermined frequency. The current through the wound excitation coils 110 creates a magnetic field. The flux from this magnetic field is coupled in the fluid passage 120. As the flux enters the fluid passage 120, eddy currents created in the electrically conductive tube 122 heat the tube which then transfers that heat to the fluid in the passage. The inductive heating of the heating element heats the fluid to a desirable temperature range in a rapid manner. In order for eddy currents to be created by magnetic coupling, the tube 122 is preferably made of an electrically conductive material, such as stainless steel. The frequency used can be any suitable frequency, e.g., in the range between 20 KHz to 1 MHz. The frequency is determined based upon the desired skin depth heating zone. For example, if the walls of the tube are very thin, then the amount of penetration in the skin is very minimal and thus a higher frequency can be used than in the case where the walls of the tube are thick.

An air gap 140 is also shown in the inductive heater of FIG. 1. This air gap serves the purpose of thermally insulating the heated fluid passage 120. The air gap is preferably sized to accommodate thermal isolation and coupled power requirements, e.g., a smaller gap provides more efficient coupled power transfer to the target but less thermal isolation. If the coil bobbin 130 was in contact with the fluid passage 120, then the coil bobbin 130 could create a heat sink and draw heat away from the fluid passage 120, thereby decreasing the efficiency of the heating mechanism.

The excitation coils 110 in FIG. 1 can be wound around the coil bobbin 130 in various configurations in order to operate under different design conditions. For example, the density of the excitation coils 130 on the right side of the coil bobbin 130 can be increased and decreased on the left side in order to create a greater concentration of flux at the right side than on the left and thus greater heating ability on the upstream portion of the fluid passage. Likewise, for an opposite effect, the density of coils at the downstream portion of the fluid passage could be greater than at the upstream end.

Figure 3:
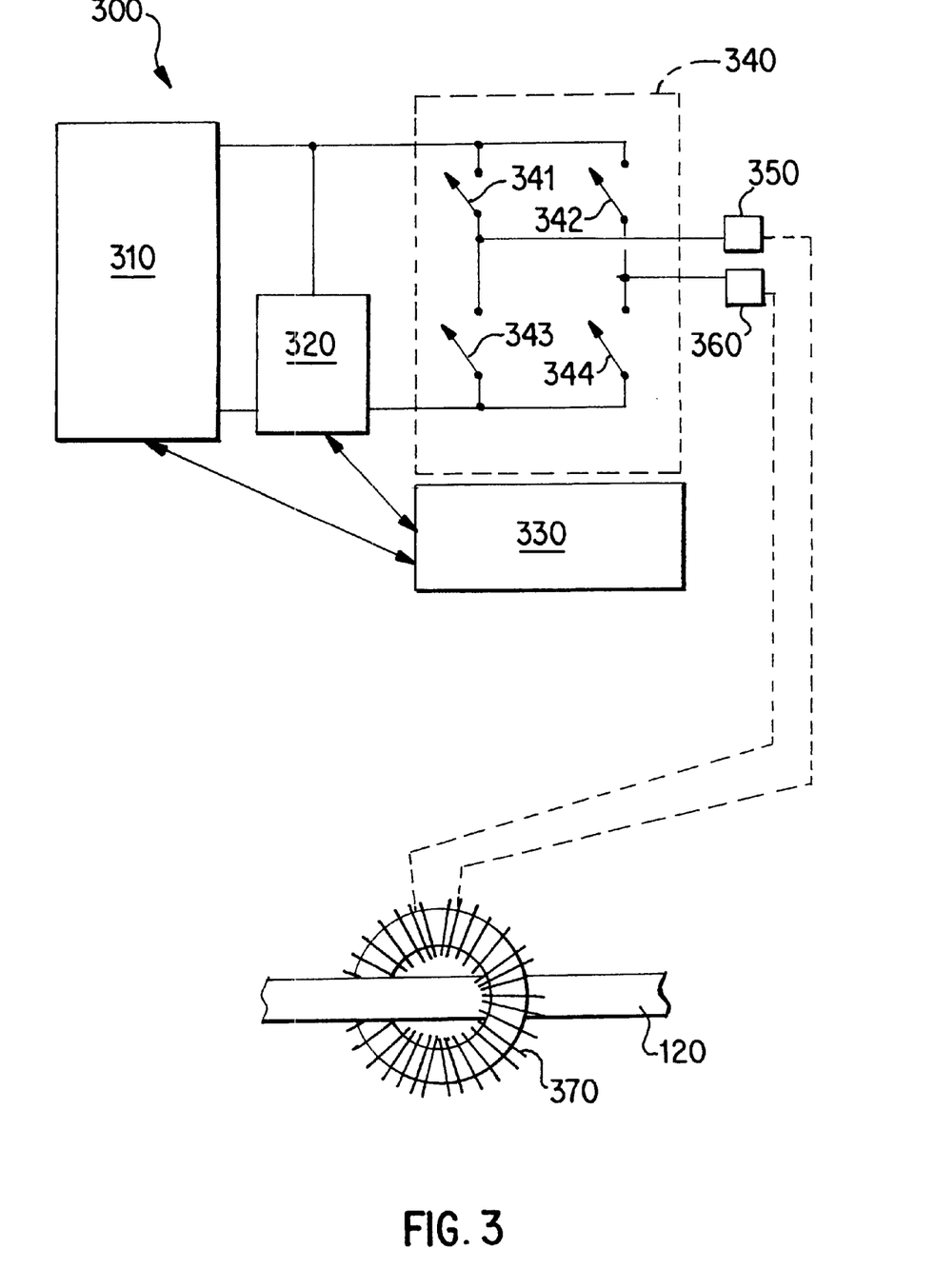
FIG. 3 is an exemplary embodiment of a control circuit for use with an inductive heater.

Advantages of using inductive heating include simplicity in design in targeting a specified region of the fluid passage 120 and the ability to provide uniform heating to the targeted area. Preferred tube shapes for providing this uniform heating in inductive heating applications in the fluid passage 120 include circular, oval and polygonal (e.g., square shaped) tube shapes. In a circular tubular shape the eddy currents created are relatively uniform around the region being heated, thus creating a uniformly heated region. Polygonal shapes can also provide relatively uniform heating despite a slightly higher increase in temperature in the corners of the tube.

One advantage of the inductive heater is it's adaptability. That is, because heating of fluids in the fluid passage may lead to buildup of particles on the inner walls of the passage 120 creating an obstruction, it may be desirable from time to time to replace the tube 122 of an aerosol device with another tube. With such an arrangement, the aerosol generator could be used to form aerosols from different fluid chemistries, e.g., fluids containing different medicaments. Thus, the tube 122 can be designed so that it can be removed from the aerosol generator and replaced with another tube of the same or different dimensions.

Another way to utilize inductive heating is to use a toroid geometry such as that shown in FIG. 2 instead of a solenoid geometry. The inductive heater of FIG. 2 can be operated in a manner similar to the inductive heater of FIG. 1 except that it uses a toroid 250 instead of a solenoid. The coil bobbin 230 holds the toroid 250 in the appropriate position and the fluid passage 120 is located through the center of the coil bobbin 230 and toroid 250, e.g., tube 120 is fitted in seals 260. The excitation coils 210 are wrapped around the core of the toroid 250. The core of the toroid 250 is preferably made of soft iron or ferrite materials in order to enhance the flux concentration. It should be noted that other coil designs, besides those shown in FIGS. 1 and 2 can be used in the inductive heater. For example, the coils can be flat and spiral inward. Such spiral coils can be placed over the surface of the heating element, heating that region of the heating element.

FIG. 3 is an exemplary power circuit 300 for powering the inductive heater. The power circuit 300 is shown connected to a toroid design inductive heater. In FIG. 3, the excitation coils 370 are shown wrapped around a core and the fluid passage 120 is shown located between the center of the toroid. The power circuit shown is a FET power bridge which is just one example of various types of circuits that may be used to power the inductive heaters of the present invention. The power supply can be a 5–15 Volt DC source and a convertor can provide an AC current through the toroid. This can be accomplished by use of the switches and forcing current to flow in opposite directions to simulate AC current as seen by the toroid. For example, switches 341 and 344 turn on so that current flows through the resonant capacitor 350, through the toroid, back through the second resonant capacitor 360 and through switch 344. When switches 342 and 343 open and 341 and 344 are closed, current flows in the opposite direction. Thus, a simulation of AC current is obtained as seen by the toroid. Although a toroid inductive heater is shown in FIG. 3, a solenoid inductive heater could also be used with the power circuit.

Figure 4:
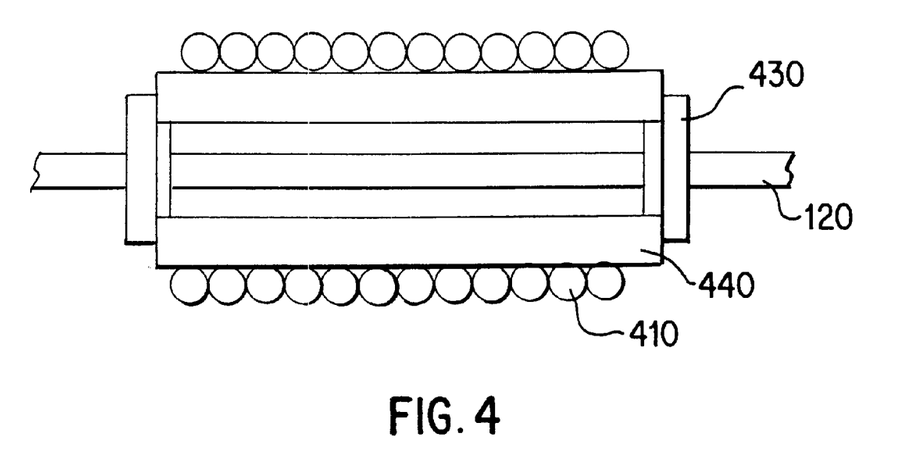
FIG. 4 is an exemplary embodiment of an inductive heater with a concentrator sleeve.

Another exemplary embodiment of an inductive heater is shown in FIG. 4. The inductive heater of FIG. 4 includes solenoidal excitation coils 410 and a flux concentrator 440. The flux concentrator 440 is positioned between the fluid passage 120 and the excitation coils 410. The shape of the flux concentrator 440 can be the same as that of the fluid passage 120, e.g. the tube 122 and the concentrator 440 can be concentric cylinders. In the embodiment shown, the flux concentrator 440 comprises a sleeve which fits on spacers 430 and the tube 122 is removably mounted in aligned openings in the spacers 430. In this way, the flux concentrator 440 is spaced a predetermined distance away from the tube 122.

The performance of the solenoidal inductive heater can be enhanced with the use of the flux concentrator 440. That is, the coupled power can be increased by two to three or more times compared to the coupled power without the flux concentrator 440. The flux concentrator 440 also further reduces EMI emissions. The flux concentrator 440 can be composed of any material that will concentrate the flux from the excitation coils 410. Preferably, a ferrite element is used as a flux concentrator because of its commercial availability and low cost.

Figure 5:
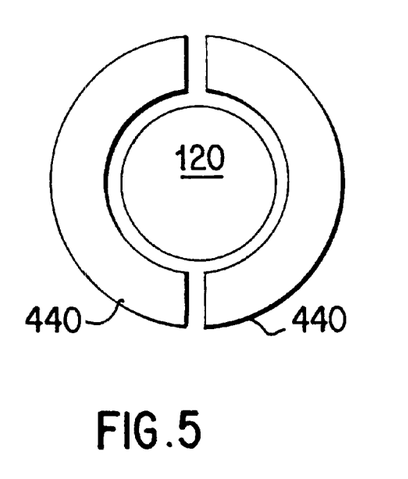
FIG. 5 is a top view of an exemplary concentrator sleeve surrounding a capillary tube.

FIG. 5 is an exemplary embodiment of the flux concentrator 440 showing the positioning of the flux concentrator 440 as it surrounds the fluid passage 120. The flux concentrator 440 can be made as one single sleeve that slides over the fluid passage 120 or it can be made of separate pieces (e.g., two semicylindrical pieces), as shown in FIG. 5, that fit together to form the sleeve.

An advantage of the inductive heater is that it can heat the fluid in passage 120 without coming into contact with the fluid, thereby avoiding contamination of the fluid and/or buildup of deposits on the heater. Further, the non-contact feature allows the heater to be used with different fluid passage designs and/or replaceable fluid conduits such as stainless steel or metal coated glass tubular fluid delivery systems.

In each of the above inductive heaters, the number of coil turns affect the heating rate and the focusing of heat on an area in the fluid passage 120. Increasing the number of coil turns will increase the amount of flux through the fluid passage 120 whereby it is possible to decrease the amount of time it takes to heat the fluid passage 120.

The principle of increasing coil turns can be applied to focus heat on one or more areas of the fluid passage 120. This is accomplished by winding more excitation coils around the area(s) where heat is to be focused. Thus, more flux can be concentrated on a specified area to provide more heat to that area.

Figure 6:
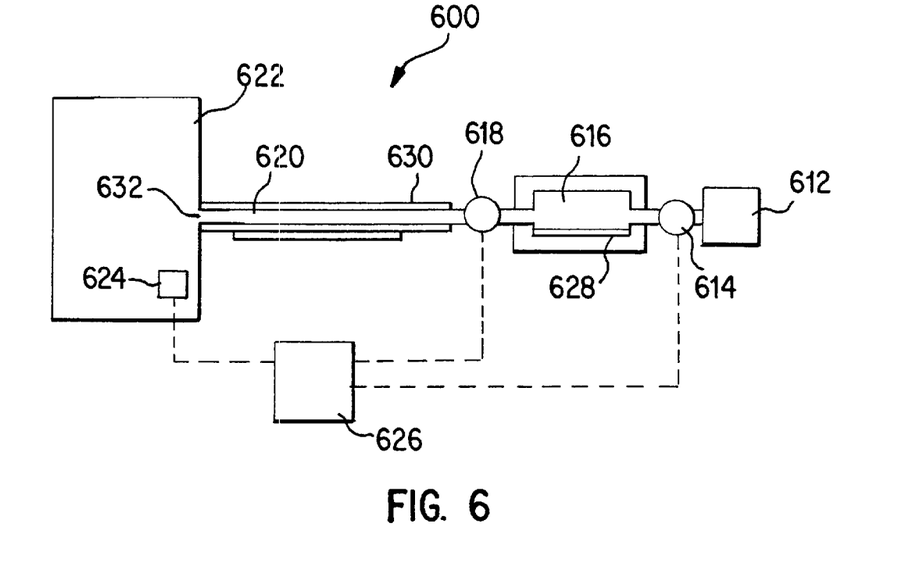
FIG. 6 is a schematic of an exemplary embodiment of an aerosol generator.
Figure 7:
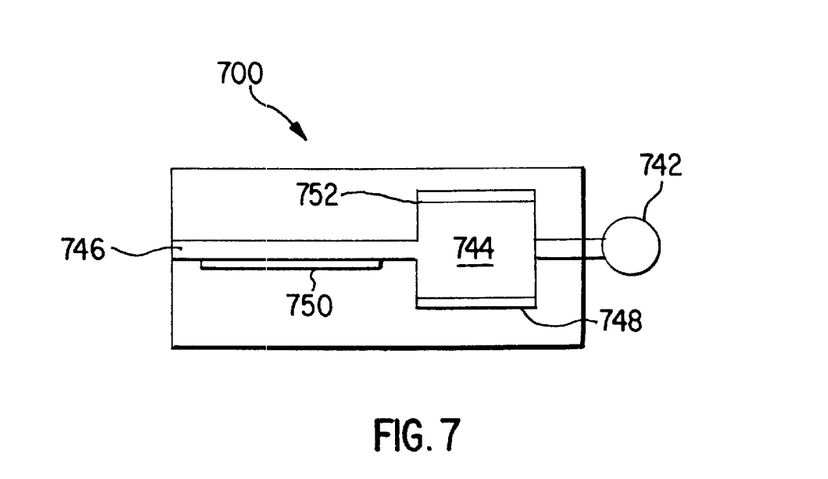
FIG. 7 is a cross section of an exemplary embodiment of an aerosol generator.

In another exemplary embodiment, the aerosol generator can be fabricated using microelectronic mechanical systems (MEMS) technology. The MEMS technology utilizes fabrication techniques that are known such as for fabrication of semiconductor devices. Using this technology, the fluid passage can comprise a channel in a multilayered composite. The layer can be of any suitable material such as metal, plastic or ceramic material. For example, the fluid passage can be etched into a layer of ceramic material such as alumina, the heating element can be formed by depositing a metal layer in the channel or on another layer of material, and the layers can be attached together by any suitable technique such as adhesive bonding, brazing, etc. The resulting composite thus provides a fluid passage by way of the channel and a heating element by way of the metal layer. The heating element can be located in an inductive excitation coil arrangement and when fluid is supplied to the channel, the excitation coil arrangement can inductively heat the heating element to vaporize the fluid.

FIG. 6 shows a vapor driven aerosol generator 600 which can incorporate the inductive heating arrangement in accordance with the invention. As shown, the aerosol generator 600 includes a source 612 of fluid, a valve 614, an optional chamber 616, a valve 618, a passage 620, a mouthpiece 622, an optional sensor 624 and a controller 626. In addition, the aerosol generator 600 includes an optional preheater element 628 and a main heater element 630. The controller 626 includes suitable electrical connections and ancillary equipment such as a battery which cooperates with the controller for operating the valves 614, 618, the sensor 624 and excitation coils for heating the heating elements 628, 630. In operation, the valve 614 can be opened to allow a desired volume of fluid from the source 612 to enter the chamber 616 during which time the valve 618 can be closed to prevent the incoming fluid from advancing into the passage 620. Filling of the chamber 616 can occur prior to or subsequent to detection by the sensor 624 of vacuum pressure applied to the mouthpiece 622 by a user attempting to inhale aerosol from the inhaler 600. Once the chamber 616 contains a predetermined volume of fluid, the controller 626 closes valve 614 and opens valve 618 while operating an excitation coil (not shown) to inductively heat the preheater element 628 to drive the fluid into the passage 620. While the fluid passes through the passage 620, the controller 626 operates another excitation coil (not shown) to inductively heat the main heater element 630 to heat the fluid to a suitable temperature for volatilizing the fluid. The volatilized fluid exits an outlet 632 of the passage 620 and the volatilized fluid forms an aerosol which can be inhaled by a user drawing upon the mouthpiece 622.

FIG. 7 shows a top cut-away view of a vapor driven aerosol generator 700 in accordance with another embodiment of the invention. As shown, the aerosol generator 700 includes a fluid supply 742, a chamber 744, a fluid passage 746, a preheater element 748 and a main heater element 750. The preheater element 748 can be arranged on one side of the chamber 744 such that fluid in the chamber 744 is heated to form a vapor bubble which expands and drives the remaining fluid in the chamber 744 into the passage 746. If desired, an additional preheater element 752 can be provided in the chamber 744 in order to provide additional heating of the fluid. The main heater element 752 can be inductively heated by an excitation coil (not shown) to form a volatilized fluid which exits the passage 746 and forms an aerosol.

Further, operation of the excitation coils and supply of fluid from the fluid source 742 can be controlled by a suitable controller as shown in the embodiment of FIG. 6.

While this invention has been described in conjunction with the exemplary embodiments outlined above, it is evident that many alternatives, modifications and variations will be apparent to those skilled in the art. Accordingly, the exemplary embodiments of the invention may be made without departing from the spirit and scope of the invention.

What is claimed is:

1. An aerosol generator, comprising:
   a capillary fluid passage having an upstream end adapted to receive fluid from a fluid supply; and
   an inductive heater comprising at least one excitation coil and at least one heating element located along the fluid passage, the excitation coil being adapted to form an electromagnetic field which causes the heating element to heat fluid in the fluid passage such that the fluid is vaporized and forms an aerosol after exiting the fluid passage.

2. The aerosol generator of claim 1, wherein the excitation coil comprises a solenoid coil or the coil is toroidal shaped.

3. The aerosol generator of claim 1, wherein the heating element comprises an electrically conductive tube.

4. The aerosol generator of claim 3, wherein the tube is made of stainless steel.

5. The aerosol generator of claim 1, wherein the fluid passage is a channel in a composite.

6. The aerosol generator of claim 1, wherein the vaporized fluid exits at one end of the fluid passage through a restricted opening.

7. The aerosol generator of claim 1, wherein the excitation coil is located adjacent a downstream end of the fluid passage.

8. The aerosol generator of claim 1, wherein the excitation coil is driven by an electronic driver circuit.

9. The aerosol generator of claim 8, wherein the electronic driver circuit is powered by 5–15 volts.

10. The aerosol generator of claim 1, wherein the fluid passage is located in a multilayered composite.

11. The aerosol generator of claim 1, further comprising:
    a mouthpiece through which a user inhales the aerosol; and
    a pressure sensor adapted to detect a vacuum pressure applied to the mouthpiece by the user.

12. The aerosol generator of claim 1, further comprising:
    a valve operable to control entry of the fluid into the fluid passage from the fluid supply; and
    a controller operable to control the operation of the valve.

13. An aerosol generator, comprising:
    a fluid passage extending through a tube removably mounted in the aerosol generator, the fluid passage having an upstream end adapted to receive fluid from a fluid supply; and
    an inductive heater comprising at least one excitation coil and at least one heating element located along the fluid passage, the excitation coil being adapted to form an electromagnetic field which causes the heating element to heat fluid in the fluid passage such that the fluid is vaporized and forms an aerosol after exiting the fluid passage.

14. An aerosol generator, comprising:
    a fluid passage having an upstream end adapted to receive fluid from a fluid supply; and
    an inductive heater comprising at least one excitation coil wound on a bobbin surrounding the fluid passage and at least one heating element located along the fluid passage, the excitation coil being adapted to form an electromagnetic field which causes the heating element to heat fluid in the fluid passage such that the fluid is vaporized and forms an aerosol after exiting the fluid passage.

15. An aerosol generator, comprising:
    a fluid passage having an upstream end adapted to receive fluid from a fluid supply;
    an inductive heater comprising at least one excitation coil and at least one heating element located along the fluid passage, the excitation coil being adapted to form an electromagnetic field which causes the heating element to heat fluid in the fluid passage such that the fluid is vaporized and forms an aerosol after exiting the fluid passage; and
    a flux concentrator positioned so as to increase the amount of flux created by the electromagnetic field that passes through the heating element.

16. The aerosol generator of claim 15, wherein the flux concentrator is positioned between the excitation coil and fluid passage.

17. The aerosol generator of claim 15, wherein the flux concentrator is made of multiple pieces of flux concentrating material that extend around the heating element.

18. The aerosol generator of claim 15, wherein the flux concentrator is made of a single piece of flux concentrating material that surrounds the heating element.

19. A method for generating an aerosol, comprising:
    supplying fluid to a capillary fluid passage in which fluid flows from an upstream end of the fluid passage to a downstream end of the fluid passage;
    heating a heating element by induction heating such that fluid in at least a portion of the fluid passage is vaporized; and
    expanding the vaporized fluid out of the fluid passage and forming an aerosol.

20. The method of claim 19, wherein the heating is carried out using a solenoidal coil or a toroidal coil.

21. The method of claim 19, wherein the vaporized fluid passes through a small outlet at the downstream end of the fluid passage.

22. The method of claim 19, wherein the capillary tube comprises an electrically conductive material and the heating is carried out by inductively generating eddy currents on a surface of the capillary tube.

23. The method of claim 19, wherein the fluid passage is located in a multilayered composite.

24. A method for generating an aerosol, comprising:
    supplying fluid to a fluid passage extending through a tube removably mounted in an aerosol generator, the fluid flowing from an upstream end of the fluid passage to a downstream end of the fluid passage;
    heating a heating element by induction heating such that fluid in at least a portion of the fluid passage is vaporized; and
    expanding the vaporized fluid out of the fluid passage and forming an aerosol.

25. A method for generating an aerosol, comprising:
    supplying fluid to a fluid passage in which fluid flows from an upstream end of the fluid passage to a downstream end of the fluid passage;
    heating a heating element by induction heating using a flux concentrator which extends around the fluid passage such that fluid in at least a portion of the fluid passage is vaporized; and expanding the vaporized fluid out of the fluid passage and forming an aerosol.

26. A method for generating an aerosol, comprising:

supplying fluid to a fluid passage in which fluid flows from an upstream end of the fluid passage to a downstream end of the fluid passage;

heating a heating element by induction heating using a solenoidal coil or a toroidal coil such that fluid in at least a portion of the fluid passage is vaporized;

increasing the amount of flux created by the electromagnetic field that passes through the heating element with a flux concentrator; and expanding the vaporized fluid out of the fluid passage and forming an aerosol.

27. The method of claim 26, wherein the flux concentrator is positioned between the coil and fluid passage.

28. The method of claim 26, wherein the flux concentrator is made of multiple pieces of flux concentrating material that extend around the heating element.

29. The method of claim 26, wherein the flux concentrator is made of a single piece of flux concentrating material that surrounds the heating element.

* * * * *